(12) United States Patent
Hastings et al.

(10) Patent No.: US 8,663,272 B2
(45) Date of Patent: Mar. 4, 2014

(54) BIODEGRADABLE ADHESIVE FILM FOR VASCULAR CLOSURE

(75) Inventors: Roger Hastings, Maple Grove, MN (US); Michael Pikus, Golden Valley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 57 days.

(21) Appl. No.: 13/253,438

(22) Filed: Oct. 5, 2011

(65) Prior Publication Data

US 2012/0089171 A1    Apr. 12, 2012

Related U.S. Application Data

(60) Provisional application No. 61/390,804, filed on Oct. 7, 2010.

(51) Int. Cl.
*A61B 17/08* (2006.01)
(52) U.S. Cl.
USPC .......................................... 606/213; 604/265
(58) Field of Classification Search
USPC ......... 606/192, 194, 213, 214, 215, 216, 232; 604/11, 93.01, 164.01–164.04, 164.08, 604/164.09, 164.1, 164.11, 263, 264, 265; 623/1.1, 1.13, 902; 128/898
See application file for complete search history.

(56) References Cited

U.S. PATENT DOCUMENTS

| | | | |
|---|---|---|---|
| 5,431,639 A | 7/1995 | Shaw | |
| 5,976,178 A * | 11/1999 | Goldsteen et al. | 623/1.13 |
| 2003/0233120 A1 | 12/2003 | Akerfeldt | |
| 2007/0060950 A1 | 3/2007 | Khosravi | |
| 2008/0065150 A1 | 3/2008 | Drasler | |
| 2008/0215087 A1* | 9/2008 | Pavcnik et al. | 606/213 |
| 2009/0044895 A1 | 2/2009 | Fortune et al. | |

FOREIGN PATENT DOCUMENTS

WO   2009059217 A2   5/2009
WO   2010018447 A1   2/2010

* cited by examiner

*Primary Examiner* — Dianne Dornbusch
*Assistant Examiner* — Robert Lynch
(74) *Attorney, Agent, or Firm* — Seager, Tufte & Wickhem LLC (57) ABSTRACT

Devices and methods for sealing an opening in a blood vessel are disclosed. A device can include: an elongate, tubular non-stick outer sheath, the non-stick outer sheath having a distal end that is insertable into a vessel of a patient through the opening in the vessel wall, and having a proximal end remaining outside the patient; an elongate, tubular non-stick inner sheath disposed within the non-stick outer sheath; and an elongate, tubular adhesive film disposed between the non-stick outer sheath and the non-stick inner sheath, the adhesive film having both inward-facing and outward-facing adhesive surfaces and being supportable by the non-stick inner sheath during insertion into the vessel of the patient.

18 Claims, 7 Drawing Sheets

BIODEGRADABLE ADHESIVE FILM FOR VASCULAR CLOSURE

RELATED APPLICATIONS

This application claims priority to U.S. Provisional Application Ser. No. 61/390,804 filed Oct. 7, 2010.

FIELD

The present disclosure relates generally to medical devices and more particularly to biodegradable tissue adhesive film, arterial sealing and self adhesion.

BACKGROUND

There is currently research into biodegradable tissue adhesives that may be used for wound closure. For instance, a thin film sheet may be prepared, and applied to an internal organ of a patient. The sheet can seal an opening, can promote healing, and in time can degrade without significant scarring to the surrounding tissue.

There exists a need for a vessel sealing device using a biodegradable adhesive film with improved properties.

BRIEF SUMMARY

An embodiment of the present disclosure includes a device for sealing an opening in a vessel wall, including: an elongate, tubular non-stick outer sheath, the non-stick outer sheath having a distal end that is insertable into a vessel of a patient through the opening in the vessel wall, and having a proximal end remaining outside the patient; an elongate, tubular non-stick inner sheath disposed within the non-stick outer sheath; and an adhesive film disposed between the non-stick outer sheath and the non-stick inner sheath, the adhesive film having both inward-facing and outward-facing adhesive surfaces and being supportable by the non-stick inner sheath during insertion into the vessel of the patient.

Another embodiment of the present disclosure includes a device for sealing an opening in a vessel wall, including: an elongate, tubular non-stick outer sheath, the non-stick outer sheath having a distal end that is insertable into a vessel of a patient through the opening in the vessel wall, and having a proximal end remaining outside the patient; an elongate, tubular non-stick inner sheath disposed within the non-stick outer sheath; an elongate, tubular adhesive film disposed between the non-stick outer sheath and the non-stick inner sheath, the adhesive film having an outward-facing adhesive surface and being supportable by the non-stick inner sheath during insertion into the vessel of the patient; and an inflatable balloon distally advanceable and proximally retractable within the non-stick inner sheath, the balloon capable of sequentially being in a pre-inflated state, in an inflated state, and in a post-inflated state. In the pre-inflated state, a distal end of the adhesive film extends into the vessel and extends beyond the distal end of the non-stick outer sheath, and the balloon extends distally beyond a distal end of the non-stick inner sheath and beyond the distal end of the adhesive film. In the inflated state, the balloon is inflated, and the distal end of the adhesive film is flared outward from a central axis of the non-stick inner sheath. In the inflated state, a proximal force applied to the balloon and to the non-stick inner sheath adheres the flared distal end of the adhesive film to an inner surface of the vessel wall surrounding the opening in the vessel wall. In the post-inflated state, the balloon is deflated and is withdrawn proximally from the vessel of the patient, and the non-stick inner sheath is withdrawn proximally from the vessel of the patient.

A further embodiment of the present disclosure includes a method for sealing an opening in a vessel wall, including: distally advancing a catheter into a vessel of a patient through the opening in the vessel wall, the catheter including: an elongate, tubular non-stick outer sheath; an elongate, tubular non-stick inner sheath disposed within the non-stick outer sheath; and an adhesive film disposed between the non-stick outer sheath and the non-stick inner sheath, the adhesive film having both inward-facing and outward-facing adhesive surfaces; proximally retracting the non-stick outer sheath out of the patient to expose a distal portion of the adhesive film, the exposed distal portion extending out of the patient through the opening in the vessel wall and having a distal end within the vessel; distally advancing a balloon through the non-stick inner sheath to extend into the vessel; inflating the balloon, thereby outwardly flaring the distal end of the adhesive film; proximally pulling on both the inflated balloon and the non-stick inner sheath, thereby forcing the inflated balloon against an interior of the vessel wall, thereby forcing the outwardly flared distal end of the adhesive film against the vessel wall, thereby adhering the outward-facing adhesive surface of the adhesive film to the interior of the vessel wall around the perimeter of the opening; proximally retracting the non-stick inner sheath out of the patient; deflating the balloon; pinching the deflated balloon closed proximate a skin surface of the patient, thereby adhering the inward-facing adhesive surface to itself to form a seal; and cutting and removing the adhesive film proximal to the seal.

BRIEF DESCRIPTION OF THE DRAWINGS

Embodiments of the present disclosure may be more completely understood in consideration of the following detailed description of the various embodiments in connection with the accompanying drawings, in which.

While the devices and methods described herein are amenable to various modifications and alternative forms, specifics thereof have been shown by way of example in the drawings and will be described in detail. It should be understood, however, that the intention is not to limit the devices and methods to the particular embodiments described. On the contrary, the intention is to cover all modifications, equivalents, and alternatives falling within the spirit and scope of the devices and methods described herein.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.718, 3, 3.14159265, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

A non-limiting example of a specific embodiment of a device and method for sealing an opening in a blood vessel follows. In this non-limiting example, a catheter includes non-stick inner and non-stick outer sheaths, with an adhesive film disposed between the sheaths. The catheter is inserted into the patient, through the opening in the blood vessel, to extend into the vessel. The non-stick outer sheath is retracted out of the patient to expose an outward-facing adhesive surface of the adhesive film, which extends from inside the vessel, through the opening in the vessel wall, to the exterior of the patient. A balloon is introduced through the non-stick inner sheath into the vessel, then is inflated. The distal end of the adhesive film is flared outward. The balloon and non-stick inner sheath are then pulled proximally together until the balloon engages the vessel wall. The outward-facing adhesive surface on the flared distal end of the adhesive film is forced against the vessel wall and forms a seal around the perimeter of the opening. The balloon is deflated and withdrawn, the non-stick inner sheath is withdrawn, and the adhesive film is sealed. The adhesive film may have an optional inward-facing adhesive surface that can be pinched against itself to seal the opening. The adhesive film is impermeable to blood and is biodegradable. There is nothing left behind when the adhesive film degrades. The preceding example is provided merely as a summary of one particular embodiment of the disclosure, and should not be construed as limiting in any way.

Figure 1:
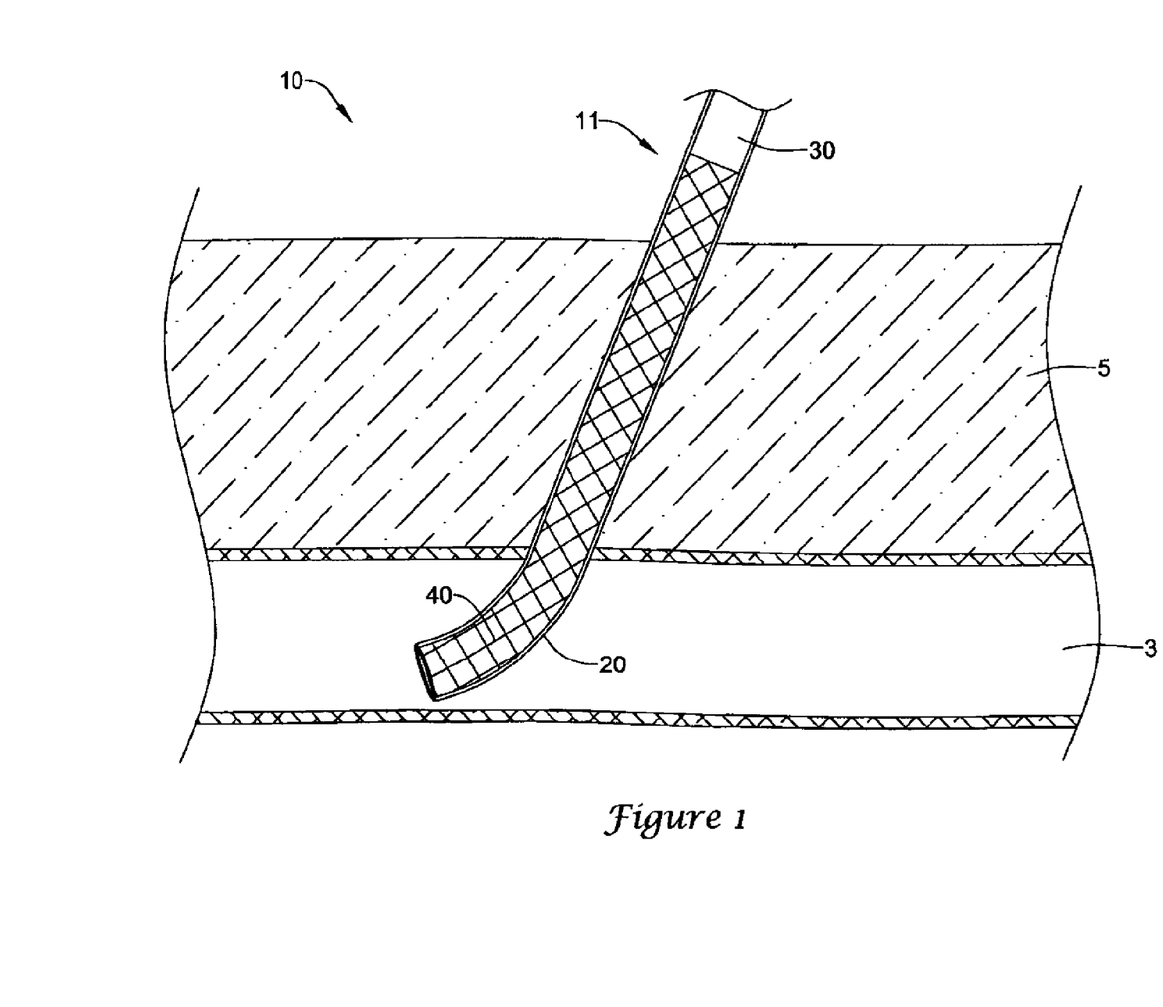
FIG. 1 is a side-view schematic drawing of an exemplary device for sealing an opening in a blood vessel.

FIG. 1 is a side-view schematic drawing of an exemplary device 10 for sealing an opening 1 in the wall 2 of a blood vessel 3. FIG. 1 shows a layer of tissue adjacent the vessel 3, which is referred to generally in this document as skin 5. The path through the tissue from the vessel wall opening 1 to the exterior of the patient may be referred to as a wound track.

In embodiments of the present disclosure, a catheter 11 is inserted into the opening 1, and includes an elongate, tubular, non-stick outer sheath 20, which may be referred to herein as a covering sheath, an elongate, tubular, non-stick inner sheath 30 within the non-stick outer sheath 20, which may be referred to as an introducer sheath, and an adhesive film 40 disposed between the non-stick inner 30 and non-stick outer 20 sheaths.

In some cases, the catheter 11 has a dedicated usage for closing and sealing the opening 1 in the vessel wall 2. In other cases, the catheter 11 may be part of another medical procedure, where elements for the procedure may be delivered through non-stick inner sheath 30. Once the procedure is completed, the catheter 11 may be used to close and seal the opening 1 in the vessel wall 2, just as if the catheter were used exclusively for closing and sealing.

The outer or covering sheath 20 may have a distal end 21 that is inserted through the opening 1 in the vessel wall 2 into the vessel 3, and a proximal end (not shown) that remains outside the patient. The non-stick outer sheath 20 may be made from a non-stick material, such as Teflon, and/or may include one or more lubricious coatings on its interior and/or exterior surfaces. In general, the term non-stick outer sheath 20 refers to a sheath that may be advanced distally and/or retracted proximally with respect to elements within the non-stick outer sheath 20 or surrounding the non-stick outer sheath 20, as well as tissue that may be surrounding the non-stick outer sheath 20.

The non-stick outer sheath 20 may be made of conventional materials such as HDPE, Nylon, polyamides, or any suitable polymer. For instance, polyether block amide (PEBA) is commercially available as PEBAX® from Atochem Inc in Glen Rock, N.J.

Similarly, the non-stick inner or introducer sheath 30 may have a distal end 31 that is insertable into the vessel 3 and has a proximal end (not shown) that remains outside the patient. The non-stick inner sheath 30 may be constructed in a similar manner to the non-stick outer sheath 20, and may be made from same material or materials as the non-stick outer sheath 20. Similarly to the non-stick outer sheath 20, the non-stick inner sheath 30 may be advanced distally and/or retracted proximally with respect to elements within the non-stick inner sheath 30 or surrounding the non-stick inner sheath 30.

The adhesive film 40 may be elongate and generally cylindrical and may be disposed between the non-stick inner 30 and outer 20 sheaths. The adhesive film 40 may have an outward-facing adhesive surface, which can face the interior of the non-stick outer sheath 20 in the initial configuration of the catheter 11. In some cases, the adhesive film 40 also has an inward-facing adhesive surface, which faces the exterior of the non-stick inner sheath 30. In all cases, the adhesive in the adhesive film 40 is intended to stick to tissue, such as the inside surface of a vessel wall 2 and the wound track, and is not intended to stick to the inner 30 and outer 20 sheaths.

There is currently a significant amount of research into materials that adhere to particular kinds of human tissue. In most cases, films that are adhesive to tissue are formed as multi-layer structures, with the material or materials for each layer being chosen carefully for particular characteristics. Many of these tissue-adhesive structures are also biodegradable, and are suitable for use in the present device.

A non-limiting example of a suitable adhesive film 40 is disclosed in United States Patent Application Publication No. 2009/0044895, published on Feb. 19, 2009 as "Tissue-Adhesive Materials" to Fortune et al, the disclosure of which is incorporated by reference herein in its entirety. Fortune discloses a multi-lamellar tissue-adhesive sheet that has a structural layer or laminate conjoined to a tissue-contacting layer. The structural layer or laminate has one or more synthetic polymers having film-forming properties, and the tissue-contacting layer of material contains tissue-reactive groups. The synthetic polymers having film-forming properties are preferably biodegradable polyesters, and the tissue-reactive groups are most preferably NHS-ester groups.

The above-cited Published Patent Application of Fortune discloses one particular exemplary adhesive film 40, but other suitable single-sided or double-sided biodegradable, adhesive film 40 may also be used.

In most cases, the adhesive film 40 is significantly more flexible than the non-stick inner 30 and outer 20 sheaths, so that the adhesive film 40 is supported by the non-stick inner 30 and/or non-stick outer 20 sheaths during insertion of the catheter 11 into the vessel 3.

In FIG. 1, the state of the device 10 is shown before, during or after any suitable medical procedure that uses instruments delivered through the non-stick inner sheath 30, but is prior to any sealing of the opening 1 in the vessel wall 2. Once a practitioner begins closing and sealing the opening 1, the stages depicted in FIGS. 2-6 show the sequential states of the device 10.

Figure 2:
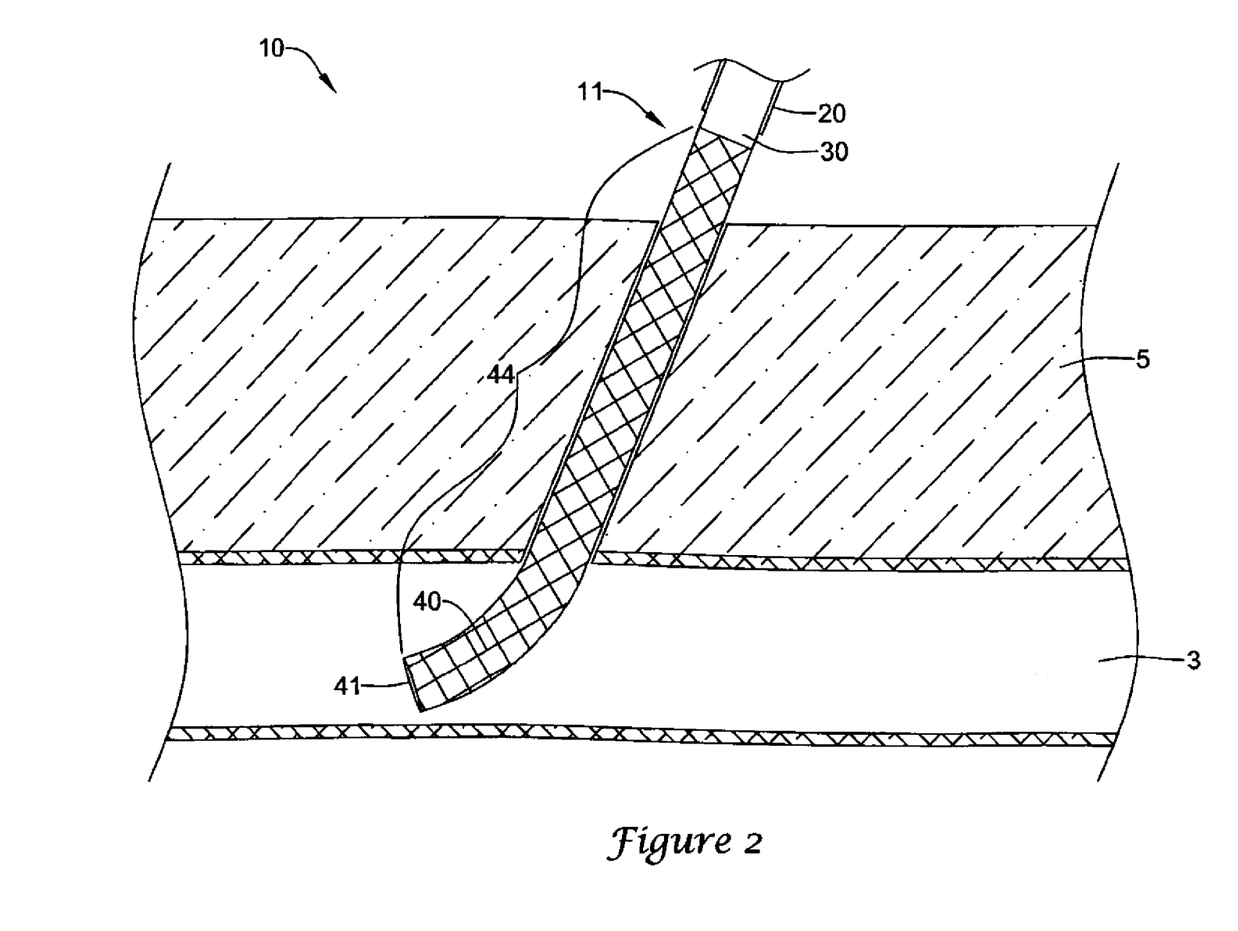
FIG. 2 is a side-view schematic drawing of the vessel sealing device of FIG. 1 with the non-stick outer sheath proximally retracted.

FIG. 2 is a side-view schematic drawing of the vessel sealing device of FIG. 1 with the non-stick outer sheath 20 proximally retracted. Such a proximal retraction is referred to herein as being "withdrawn" or "pulled back". The non-stick outer sheath 20 is retracted fully out of the patient, so that the outward-facing adhesive surface of the adhesive film 40 is exposed from within the vessel 3, through the opening 1 in the vessel wall 2, through the tissue in the wound track, and out of the body of the patient, to a point proximal to the surface of the skin of the patient.

In terms of regions along the adhesive film 40, a "distal tip" 41 is at the distal end of the adhesive film 40 and is shown in FIG. 2 extending into the vessel 3, while a "distal portion" 44 includes the adhesive-exposed portion shown in FIG. 2 and extends from the distal end proximally to a point proximal to the surface of the skin of the patient.

In some cases, the non-stick inner sheath 30 is withdrawn before the non-stick outer sheath 20 is withdrawn. In other cases, the non-stick inner sheath 30 is left extending into the vessel 3 while the non-stick outer sheath 20 is withdrawn.

Figure 3:
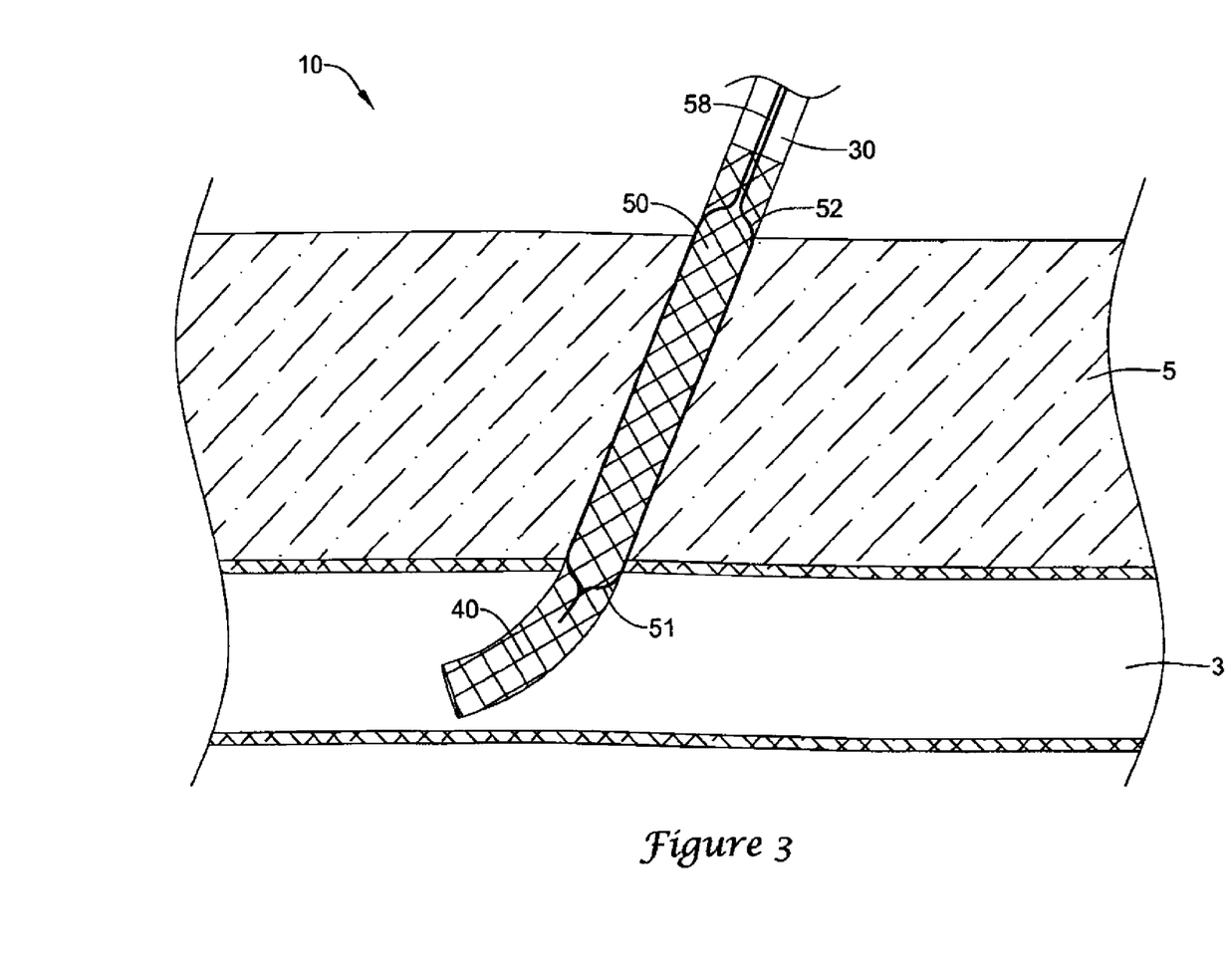
FIG. 3 is a side-view schematic drawing of the vessel sealing device of FIGS. 1-2 with the balloon partially advanced along the non-stick inner sheath.

FIG. 3 depicts a step that may or may not be used, depending on how robustly the adhesive film 40 adheres to the tissue in the wound track. If the tissue is sufficiently elastic, the tissue can spring back after the non-stick outer sheath 20 is withdrawn to engage and adhere to the adhesive film 40.

However, if the tissue is not sufficiently elastic, the practitioner may introduce a balloon 50 into the non-stick inner sheath 30, and partially advance the balloon 50 through the non-stick inner sheath 30 so that a distal end 51 of the balloon 50 extends into the vessel 3 while a proximal end 52 of the balloon 50 remains outside the patient. When the balloon 50 is advanced so that it subtends much or all of the wound track, the balloon 50 may be inflated within the non-stick inner sheath 30 through an inflation lumen 58. The inflated balloon 50 forces the adhesive film 40 radially outward against the tissue in the wound track, thereby adhering the outward-facing adhesive surface of the adhesive film 40 to adjacent tissue. The balloon 50 is then partially or fully deflated through the inflation lumen 58.

Figure 4:
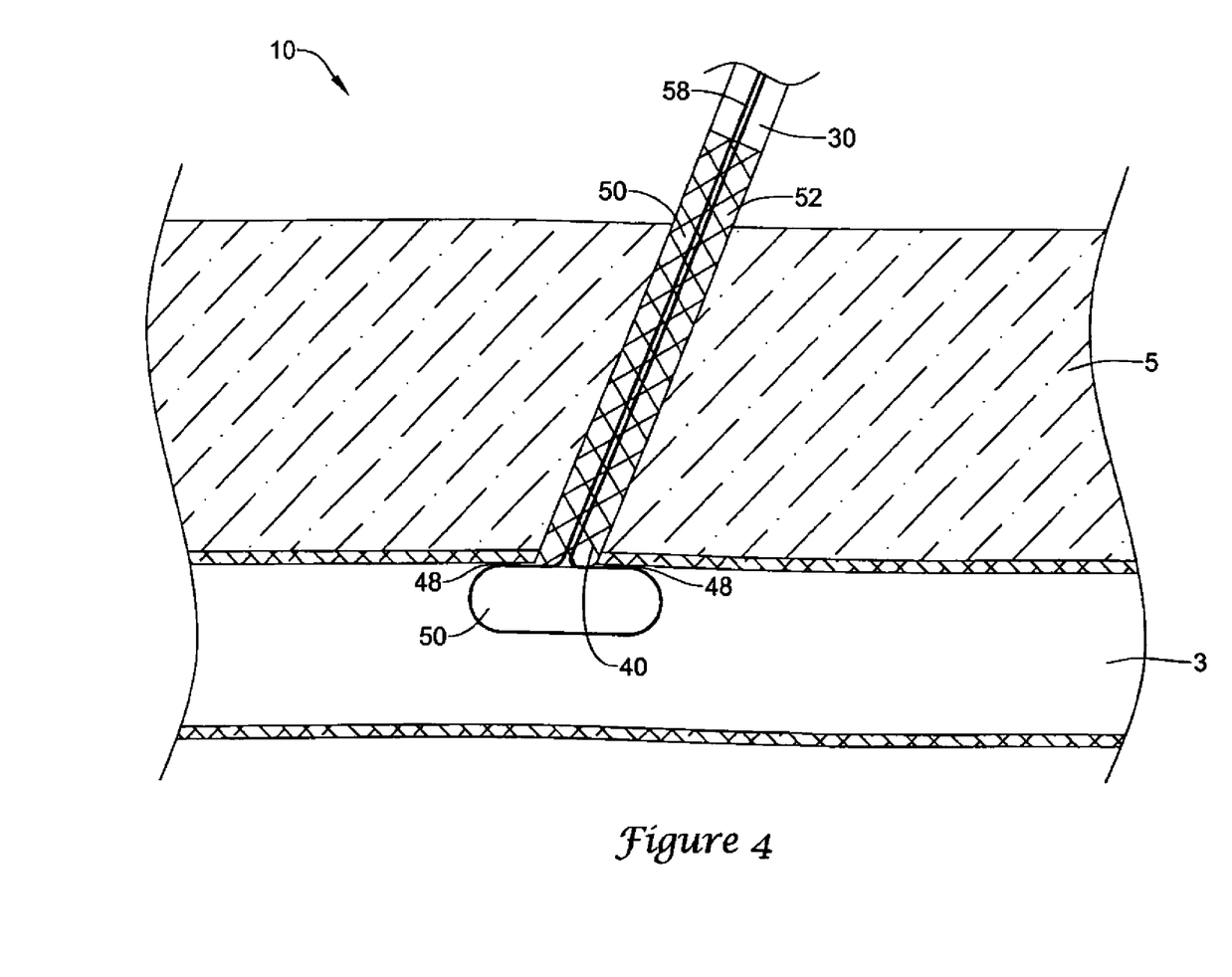
FIG. 4 is a side-view schematic drawing of the vessel sealing device of FIGS. 1-3 with the balloon inflated inside the vessel.

FIG. 4 is a side-view schematic drawing of the vessel sealing device of FIGS. 1-3 with the balloon 50 inflated inside the vessel 3. The balloon 50 in FIG. 4 may be the same balloon 50 shown in FIG. 3, or may be a different balloon 50. If the same balloon 50 is used in the later step, the deflated balloon 50 may be distally advanced to extend mostly or fully into the vessel 3. If a different balloon 50 is used in the later step, the balloon 50 of FIG. 3 may be proximally withdrawn from the non-stick inner sheath 30 once it has been deflated, a new balloon 50 may be inserted into the non-stick inner sheath 30 and distally advanced into the vessel 3.

In the step shown in FIG. 4, the balloon 50 may be distally advanced along the non-stick inner sheath 30 so that it extends past the distal end of the non-stick inner sheath 30 and past the distal end of the adhesive film 40 to extend largely or fully into the vessel 3. The inflation lumen 58 (not shown in FIG. 4) may extend proximally from the balloon 50 through the non-stick inner sheath 30. The balloon 50 may then be inflated.

The adhesive film 40 may have a flared distal end 48 that flares outward from a central axis of the non-stick inner sheath 30, much like the bell of a trumpet. Such a flaring may be caused or amplified by the inflation of the balloon 50, which may radially expand the distal end 48 of the adhesive film 40. Alternatively, the distal end 48 of the adhesive film 40 may be pre-flared or over-sized, compared with the external diameter of the non-stick inner sheath 30, prior to inflation of the balloon 50.

Once the balloon 50 is inflated, the balloon 50 and the non-stick inner sheath 30 are together pulled proximally until the balloon 50 firmly engages the inside of the wall 2 of the blood vessel 3. When the balloon 50 engages the vessel wall 2, it forces the flared distal end 48 of the adhesive film 40 against the vessel wall, so that the outward-facing adhesive surface adheres to the inner surface of the vessel wall 2 surrounding the opening 1 in the vessel wall 2.

After the flared distal end 48 of the adhesive film 40 is affixed to the vessel wall 2, the balloon 50 may be deflated and withdrawn proximally out of the patient, and the non-stick inner sheath 30 may also be withdrawn from the patient. The adhesive film 40 may then be left bonded into the wound track, forming a continuous blood barrier from the inside of the vessel wall 2 to the opening of the wound at the body surface.

Figure 5:
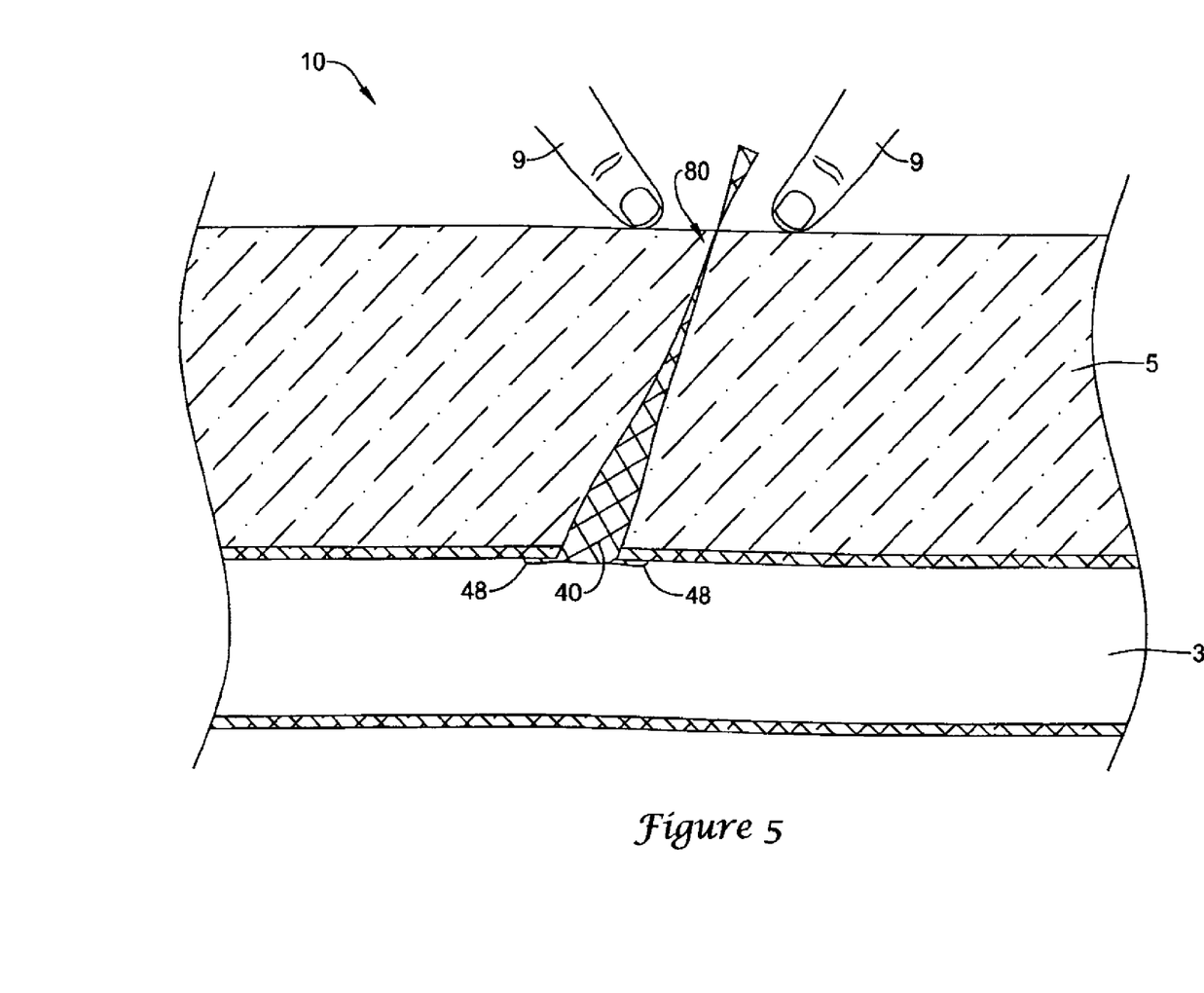
FIG. 5 is a side-view schematic drawing of the vessel sealing device of FIGS. 1-4 with the balloon deflated and removed, the non-stick inner sheath removed, and the adhesive film pinched shut.

To seal the adhesive film 40, the practitioner may pinch with fingers 9 the skin of the patient together, thereby adhering the inward-facing surface of the adhesive film 40 to itself and closing the wound. The pinched and self-adhered adhesive film 40 forms a seal 80 proximate the skin of the patient. FIG. 5 is a side-view schematic drawing of the vessel sealing device of FIGS. 1-4 with the balloon 50 deflated and removed, the non-stick inner sheath 30 removed, and the adhesive film 40 pinched shut. Note that the possibility for hemotoma is greatly reduced if the seal around the perimeter of the opening 1 in the vessel wall 2 is effective and the adhesive film 40 is impermeable to blood.

In some embodiments, the inward-facing adhesive surface may be omitted. In such instances, the pinching step may be omitted and, the excess adhesive film 40 may be tied off on the outside of the patient or otherwise sealed at the opening of the wound.

Figure 6:
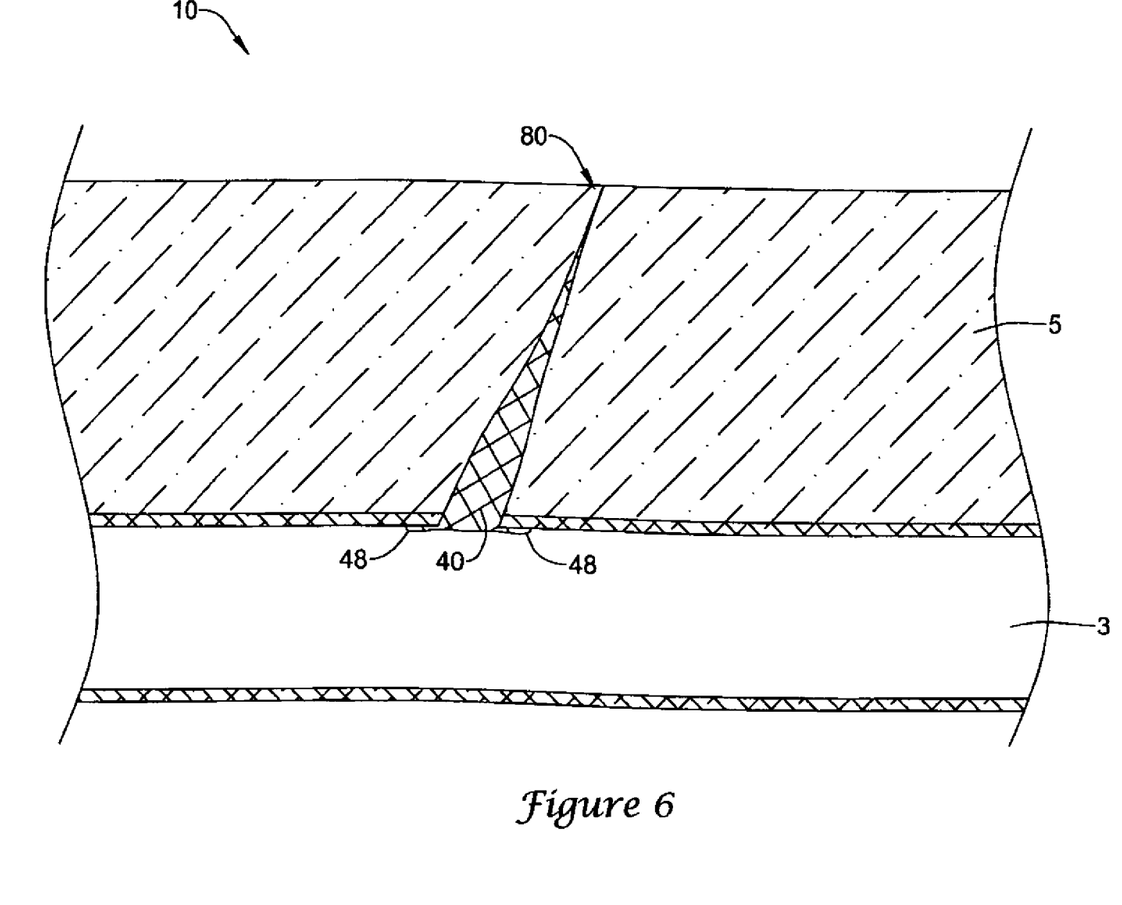
FIG. 6 is a side-view schematic drawing of the vessel sealing device of FIGS. 1-5 with the adhesive film cut off proximal to the seal.

As a final step, the excess adhesive film 40 exiting the body maybe removed, typically proximal to the seal 80, which is often near the top of the wound track. FIG. 6 is a side-view schematic drawing of the vessel sealing device of FIGS. 1-5 with the adhesive film 40 cut off proximal to the seal 80. Blood 7 that is in the lower wound tract may clot in a short period of time. In some embodiments, the adhesive film 40 may biodegrade in a matter of days.

In many cases, it may be useful for the practitioner to know how deeply into the vessel 3 the non-stick inner sheath 30 and/or the non-stick outer sheath 20 extends. Two such mechanisms for determining depth are shown in FIGS. 7 and 8.

Figure 7:
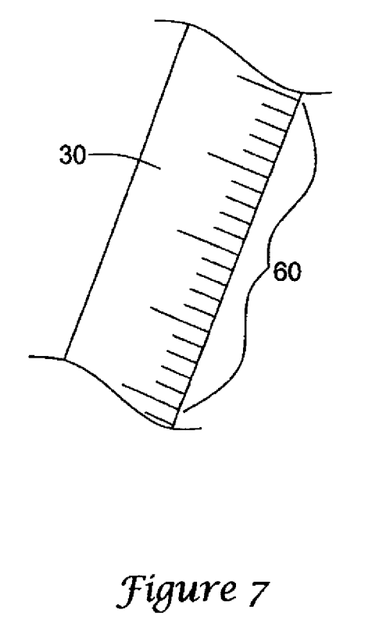
FIG. 7 is a side-view schematic drawing of a sheath having markings that indicate a certain fixed length of sheath remaining in the patient.

FIG. 7 is a side-view schematic drawing of a sheath 30 having markings that indicate a certain fixed length of sheath remaining in the patient. The markings 60 are shown on the non-stick inner sheath 30, but are equally applicable to the non-stick outer sheath 20. Such markings can be similar to those used on a ruler, with increments in millimeters, inches or fractions of an inch, and/or other suitable units of distance. The markings 60 may be printed on the exterior of the sheath 30 with a suitable bio-safe ink and/or may extend into or out of the exterior surface of the sheath 30.

Figure 8:
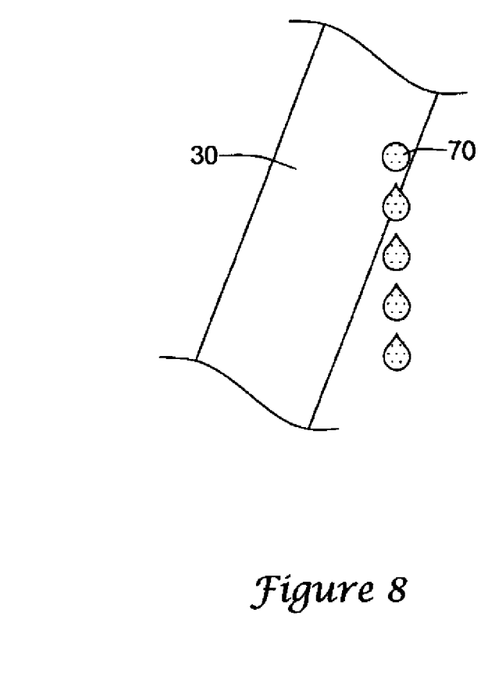
FIG. 8 is a side-view schematic drawing of a sheath having a locating hole through which blood flows when the sheath extends too far distally into the vessel.

FIG. 8 is a side-view schematic drawing of a sheath 30 having a locating hole 70 through which blood may flow when the sheath 30 extends too far distally into the vessel. The practitioner may determine readily the depth of the sheath 30 with respect to the vessel, from the appearance or disappearance of blood drops at the hole 70.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A device for sealing an opening in a vessel wall, comprising:
    an elongate, tubular non-stick outer sheath, the non-stick outer sheath having a distal end that is insertable into a vessel of a patient through the opening in the vessel wall, and having a proximal end remaining outside the patient;
    an elongate, tubular non-stick inner sheath disposed within the non-stick outer sheath; and
    an elongate, tubular adhesive film disposed between the non-stick outer sheath and the non-stick inner sheath, the adhesive film having both inward-facing and outward-facing adhesive surfaces and being supportable by the non-stick inner sheath during insertion into the vessel of the patient.

2. The device of claim 1, further comprising an inflatable balloon distally advanceable and proximally retractable within the non-stick inner sheath, the balloon capable of sequentially being in a pre-inflated state, an inflated state, and a post-inflated state.

3. The device of claim 2, wherein in the pre-inflated state, a distal end of the adhesive film extends into the vessel and extends beyond the distal end of the non-stick outer sheath, and the balloon extends distally beyond a distal end of the non-stick inner sheath and beyond the distal end of the adhesive film.

4. The device of claim 3, wherein in the inflated state, the balloon is inflated, and the distal end of the adhesive film is flared outward from a central axis of the non-stick inner sheath.

5. The device of claim 4, wherein in the inflated state, a proximal force applied to the balloon and to the non-stick inner sheath adheres the flared distal end of the adhesive film to an inner surface of the vessel wall surrounding the opening in the vessel wall.

6. The device of claim 5, wherein in the post-inflated state, the balloon is deflated and is withdrawn proximally from the vessel of the patient, the non-stick inner sheath is withdrawn proximally from the vessel of the patient, and the inward-facing adhesive surface of the adhesive film is stuck to itself to seal the opening in the vessel.

7. The device of claim 6,
    wherein the inward-facing adhesive surface of the adhesive film is stuck to itself proximate a skin surface of the patient to form a seal; and
    wherein the adhesive film is cut and removed proximal to the seal.

8. The device of claim 1, wherein at least one of the inner and non-stick outer sheaths includes at least one mark that indicates a certain fixed length of sheath remaining in the patient.

9. The device of claim 1, wherein at least one of the inner and non-stick outer sheaths includes at least one locating hole through which blood flows when the sheath extends too far distally into the vessel.

10. The device of claim 1, wherein the adhesive film is impermeable to blood.

11. The device of claim 1, wherein the adhesive film is biodegradable.

12. A device for sealing an opening in a vessel wall, comprising:
    an elongate, tubular non-stick outer sheath, the non-stick outer sheath having a distal end that is insertable into a vessel of a patient through the opening in the vessel wall, and having a proximal end remaining outside the patient;
    an elongate, tubular non-stick inner sheath disposed within the non-stick outer sheath;
    an adhesive film disposed between the non-stick outer sheath and the non-stick inner sheath, the adhesive film having an outward-facing adhesive surface and being supportable by the non-stick inner sheath during insertion into the vessel of the patient; and
    an inflatable balloon distally advanceable and proximally retractable within the non-stick inner sheath, the balloon capable of sequentially being in a pre-inflated state, then in an inflated state, then in a post-inflated state;
    wherein in the pre-inflated state, a distal end of the adhesive film extends into the vessel and extends beyond the distal end of the non-stick outer sheath, and the balloon extends distally beyond a distal end of the non-stick inner sheath and beyond the distal end of the adhesive film;
    wherein in the inflated state, the balloon is inflated, and the distal end of the adhesive film is flared outward from a central axis of the non-stick inner sheath;
    wherein in the inflated state, a proximal force applied to the balloon and to the non-stick inner sheath adheres the flared distal end of the adhesive film to an inner surface of the vessel wall surrounding the opening in the vessel wall;
    wherein in the post-inflated state, the balloon is deflated and is withdrawn proximally from the vessel of the patient, and the non-stick inner sheath is withdrawn proximally from the vessel of the patient.

13. The device of claim 12, wherein in the post-inflated state, the adhesive film is tied off outside the patient.

14. The device of claim 12, wherein in the post-inflated state, the adhesive film is sealed at the opening of the vessel wall.

15. The device of claim 12, wherein in the post-inflated state, the adhesive film is sealed exterior to the patient.

16. The device of claim 12, wherein at least one of the inner and non-stick outer sheaths includes at least one mark that indicates a certain fixed length of sheath remaining in the patient.

17. The device of claim 12, wherein at least one of the inner and non-stick outer sheaths includes at least one locating hole through which blood flows when the sheath extends too far distally into the vessel.

18. The device of claim 12, wherein the adhesive film is impermeable to blood and is biodegradable.

\* \* \* \* \*